(12) United States Patent
Prakash et al.

(10) Patent No.: US 7,672,715 B2
(45) Date of Patent: Mar. 2, 2010

(54) METHOD AND APPARATUS FOR DETERMINING EXCITATION-PHYSIOLOGIC RESPONSE DELAYS

(75) Inventors: Rajan Prakash, St. Louis Park, MN (US); Edward Chinchoy, Golden Valley, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1066 days.

(21) Appl. No.: 11/343,753

(22) Filed: Jan. 31, 2006

(65) Prior Publication Data
US 2007/0179541 A1   Aug. 2, 2007

(51) Int. Cl.
*A61B 5/04* (2006.01)
(52) U.S. Cl. .................. 600/513; 600/301; 607/18
(58) Field of Classification Search .......... 607/18; 600/301, 513
See application file for complete search history.

(56) References Cited

U.S. PATENT DOCUMENTS

| 5,213,098 | A | 5/1993 | Bennett et al. |
| 5,334,222 | A | 8/1994 | Salo et al. |
| 5,836,987 | A | 11/1998 | Baumann et al. |
| 6,044,297 | A | 3/2000 | Sheldon et al. |
| 6,070,101 | A | 5/2000 | Struble et al. |
| 6,144,880 | A | 11/2000 | Ding et al. |
| 6,221,024 | B1 | 4/2001 | Miesel |
| 6,411,848 | B2 | 6/2002 | Kramer et al. |
| 6,738,667 | B2 | 5/2004 | Deno et al. |
| 6,859,665 | B2 | 2/2005 | Ding |
| 6,871,088 | B2 | 3/2005 | Chinchoy |
| 6,882,882 | B2 | 4/2005 | Struble et al. |
| 2003/0199936 | A1 | 10/2003 | Struble et al. |
| 2005/0027320 | A1 | 2/2005 | Nehls et al. |

FOREIGN PATENT DOCUMENTS

| EP | 0219943 A2 | 4/1987 |
| WO | WO2004078257 A1 | 9/2004 |

OTHER PUBLICATIONS

International Search Report, PCT/US2007/060828, May 22, 2007, 8 Pages.

*Primary Examiner*—Carl H Layno
*Assistant Examiner*—Yun Haeng Lee
(74) *Attorney, Agent, or Firm*—Reed A. Duthler (57) ABSTRACT

An implantable medical device system and associated method are provided for measuring an excitation-physiological response delay. The method includes sensing a first signal responsive to electrical activity in a first cardiac chamber, sensing a second signal responsive to a physiologic response to the electrical activity in the first cardiac chamber; and determining an excitation-physiologic response delay in response to the first signal and the second signal.

28 Claims, 8 Drawing Sheets

METHOD AND APPARATUS FOR DETERMINING EXCITATION-PHYSIOLOGIC RESPONSE DELAYS

TECHNICAL FIELD

The invention relates generally to implantable medical devices, and, more particularly, to an implantable medical device and associated method for determining the delay between excitation of a cardiac chamber and physiologic responses to the excitation.

BACKGROUND

An excitation-physiological response delay is the time delay that occurs between excitation of excitable body tissue and a subsequent physiological response. One form of excitation-physiological response delay is the electromechanical delay (EMD) that occurs between electrical excitation of muscle tissue an the subsequent mechanical contraction. In the heart, atrial EMD is the delay between electrical activation and mechanical contraction of an atrial chamber; ventricular EMD is the delay between electrical activation and mechanical contraction of a ventricle. The inter-chamber electromechanical delay may also be defined as the delay between electrical activation of one (typically right) chamber and mechanical activation of the other (typically left) chamber. Intra-atrial EMD, as distinguished from inter-atrial EMD, can be defined as the time delay that occurs between atrial electrical activation and mechanical contraction in the same atrium. By analogy, similar definitions may be given for inter-ventricular EMD and intra-ventricular EMD. The time of electrical activation used in measuring an EMD may correspond to an intrinsic depolarization, an evoked response following a pacing pulse, or the pacing pulse.

Measurement of EMD in the heart may provide a useful diagnostic parameter (for example in classifying types of arrhythmias). EMD measurement may also be important in optimizing the synchronization of heart chambers achieved by a range of cardiac pacing therapies including cardiac resynchronization therapy (CRT). For example, measures of the intra-atrial EMD and/or inter-atrial EMD may be valuable in optimizing cardiac pacing therapy control parameters such as atrial-ventricular interval (AVI), also often referred to as the "AV delay."

DETAILED DESCRIPTION

In the following description, references are made to illustrative embodiments for carrying out the invention. It is understood that other embodiments may be utilized without departing from the scope of the invention. The invention is directed to providing a device and method for measuring excitation-physiological response delays. In particular, the invention is directed to a method and apparatus for measuring the time delay between electrical activation of cardiac tissue and a subsequent physiological response. In the illustrative embodiments presented herein, the excitation-physiologic response delay is measured as a cardiac EMD, which may be an inter-atrial EMD, and intra-atrial EMD, an inter-ventricular EMD, or an intra-ventricular EMD. However, embodiments of the invention are not limited to measuring the delay between electrical activation of a heart chamber and a subsequent mechanical event. The physiologic response may include other responses to electrical activation such as a blood pressure response or a metabolic response such as a change in blood oxygenation, pH, or other change in blood chemistry. It is to be understood that methods taught herein may be applied to any sensor signals used for detecting an excitation event and a subsequent physiological response. The measured atrial and/or ventricular EMD is used as a specific example of excitation-physiologic response delay measured for diagnostic and monitoring purposes or in optimizing cardiac pacing parameters. Furthermore, a physiologic response delay may be measured following electrical events associated with electrical depolarization as well as electrical repolarization of the cardiac tissue.

Figure 1A:
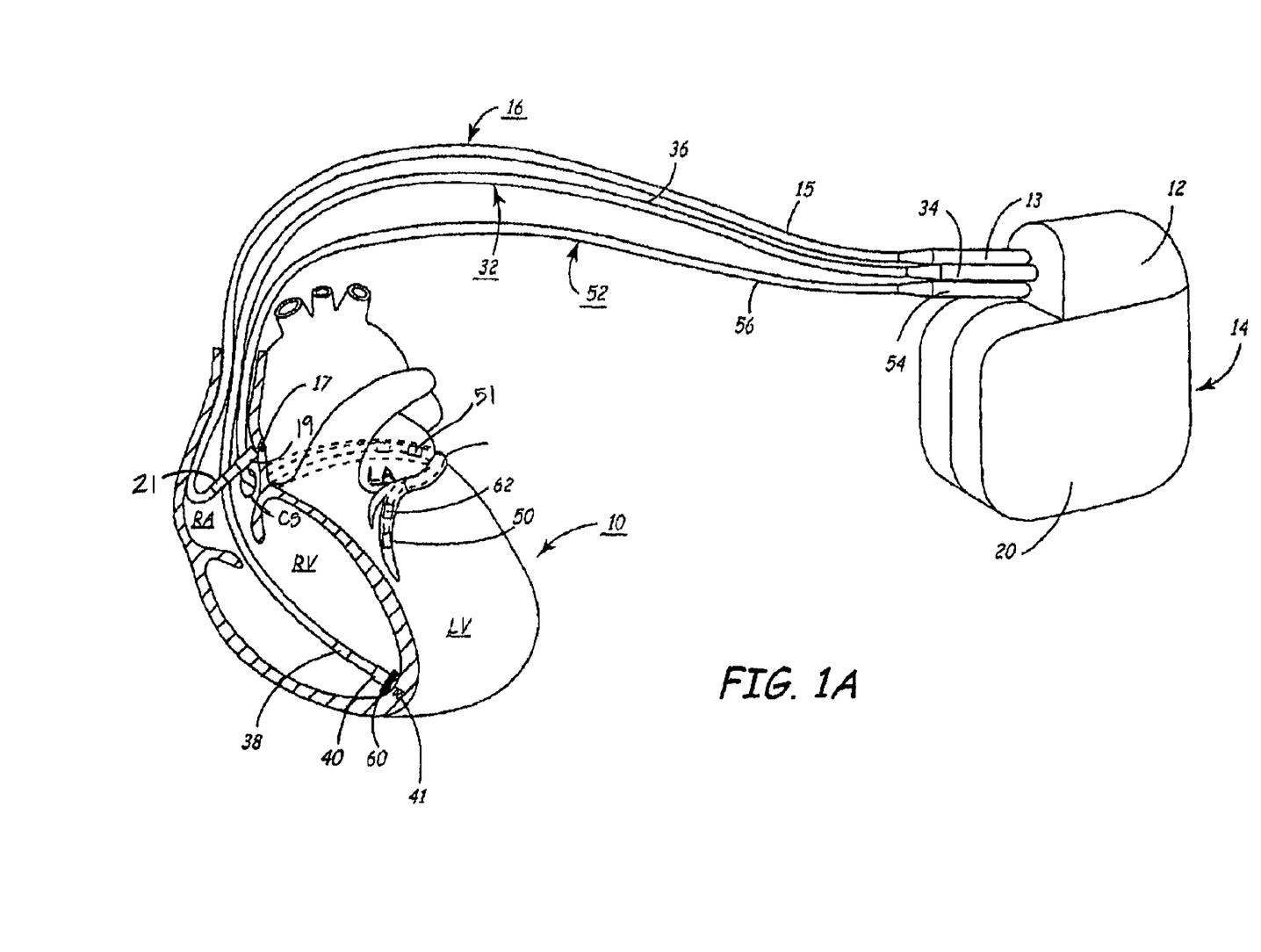
FIG. 1A depicts an implantable medical device in which one embodiment of the present invention may be implemented.

FIG. 1A depicts an implantable medical device (IMD) 14 in which one embodiment of the present invention may be implemented. IMD 14 is embodied as a multi-chamber pacemaker capable of sensing intrinsic activity of heart 10 and delivering cardiac stimulation pulses as appropriate to one or more heart chambers. IMD 14 may be programmed to operate in any of a number of therapeutic stimulation modes. For example, IMD 14 may be configured for delivering cardiac resynchronization stimulation pulses, which control the heart activation sequence for restoring mechanical synchrony between heart chambers. In other embodiments, IMD 14 may deliver extra systolic stimulation pulses as needed to achieve post-extra systolic potentiation effects and thereby provide hemodynamic benefit to the patient. In various embodiments, IMD 14 may be configured to deliver any cardiac stimulation therapy. Although IMD 14 is shown as a multi-chamber pacemaker, it is understood that IMD 14 may be modified to operate as a dual chamber, or even single chamber, pacemaker. Furthermore, in some embodiments, IMD 14 may be provided as a cardiac monitoring device configured to monitor cardiac activity and store physiological data without delivering a cardiac stimulation therapy.

IMD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. During normal conduction, the RA and LA become depolarized following spontaneous generation of an action potential by the sinoatrial node.

The inter-atrial EMD is the time interval between electrical activation of the right atrial chamber and actual mechanical contraction of the opposing left atrial chamber. Typically the inter-atrial EMD is measured as the time interval between electrical activation of the RA and mechanical contraction of the LA. Embodiments of the present invention are not limited, however, to measuring inter-atrial EMD between RA electrical activation and LA mechanical contraction. Inter-atrial EMD may also be measured using a global EGM/ECG signal representing depolarization of both atria and the mechanical contraction of either atrium. The intra-atrial EMD may be measured in either the RA or the LA as the time interval between atrial electrical activation and atrial mechanical contraction within the same chamber.

IMD 14 is typically implanted subcutaneously in a patient's body between the skin and the ribs. Three transvenous endocardial leads 16, 32 and 52 connect IMD 14 with the RA, the RV and the LV, respectively. Each lead has at least one electrical conductor and pace/sense electrode. A remote indifferent can electrode 20 is formed as part of the outer surface of the housing of the IMD 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 may be attached to the RA wall using a fixation member 17. The bipolar endocardial RA lead 16 is formed with a connector 13 fitting into a connector bore of IMD connector block 12 that is coupled to a pair of electrically insulated conductors within lead body 15 and connected with distal tip RA pace/sense electrode 19 and proximal ring RA pace/sense electrode 21 provided for achieving RA stimulation and sensing of RA electrogram (EGM) signals.

Bipolar, endocardial RV lead 32 is passed through the RA into the RV where its distal end, carrying tip RV pace/sense electrode 40 and ring RV pace/sense electrode 38, is fixed in place in the RV apex by a distal fixation member 41. The RV lead 32 is formed with a connector 34 fitting into a corresponding connector bore of IMD connector block 12 that is coupled to a pair of electrically insulated conductors within lead body 36 and connected with distal tip RV pace/sense electrode 40 and proximal ring RV pace/sense electrode 38 provided for RV stimulation and sensing of RV EGM signals. In some embodiments, RV lead 32 includes a sensor 60 responsive to RV wall acceleration. RV acceleration sensor 60 may be positioned into or proximate the RV apex for detecting acceleration of the RV apical region. In other embodiments, RV acceleration sensor 60 may be disposed at other locations along the RV for sensing RV acceleration.

Coronary sinus lead 52 is passed through the RA, into the CS and further into a cardiac vein 48 to extend the distal LV CS pace/sense electrode 50 alongside the LV chamber to achieve LV stimulation and sensing of LV EGM signals. The LV CS lead 52 is coupled at the proximal end connector 54 into a bore of IMD connector block 12. A small diameter lead body 56 is typically selected in order to lodge the distal LV CS pace/sense electrode 50 deeply in a cardiac vein branching from the great cardiac vein 48.

In one embodiment of the invention, coronary sinus lead 52 is provided with a sensor 62 capable of generating a signal proportional to the acceleration of the left ventricular free wall. Sensor 62 may be embodied as a uniaxial, biaxial, or triaxial (or multiaxial) accelerometer contained in a capsule of a relatively small size and diameter such that it may be included in a coronary sinus lead without substantially increasing the lead diameter or impairing the ability to steer the lead to a left ventricular stimulation and sensing site. For the purposes of detecting atrial mechanical contraction using an accelerometer deployed in operative relation to the left ventricle, a uniaxial accelerometer configured to generate a signal responsive to LV motion substantially along any one axis, e.g. longitudinal acceleration, may be sufficient. Sensor 62 may alternatively be provided as another type of transducer such as a transducer having an optical, acoustical, piezoelectric, inductive, capacitive, resistive, or other elements which produce a variable signal proportional to ventricular acceleration or from which variations in ventricular acceleration can be derived.

Sensor 62 is located on CS lead 52 such that when CS lead 52 is positioned for LV stimulation and sensing, sensor 62 is located over the left ventricle and is typically positioned approximately over the left ventricular free wall mid-lateral to mid-basal segments. The depicted positions of the leads and electrodes shown in FIG. 1A in or about the right and left heart chambers are approximate and merely illustrate one of many possible configurations. For example, a left ventricular acceleration sensor 62 may alternatively be located on CS lead 52 such that sensor 62 is positioned along the great cardiac vein, or along any accessible inferior cardiac vein.

In some embodiments, LV CS lead 52 could bear a proximal LA CS pace/sense electrode 51 positioned along CS lead body 56 such that it is disposed proximate the LA for use in stimulating the LA and/or sensing LA EGM signals. In that case, the lead body 56 would encase an insulated lead conductor extending proximally from the more proximal LA CS pace/sense electrode(s) and terminating at lead connector 54.

It is recognized that alternative leads and pace/sense electrodes that are adapted for intra-cardiac or subcutaneous placement may be used in conjunction with the present invention. The implantable medical device system may include housing-based electrodes and sensors as well as lead-based electrodes and sensors. In addition to or alternatively to the acceleration sensors shown in FIG. 1A, other sensors may be provided for sensing other signals responsive to physiological events that occur in response to electrical activation of a cardiac chamber. For example, pressure sensors, impedance sensors, or blood chemistry sensors such as oxygen saturation sensors and pH sensors, may be provided for detecting a physiological response to excitation of a cardiac chamber.

Figure 1B:
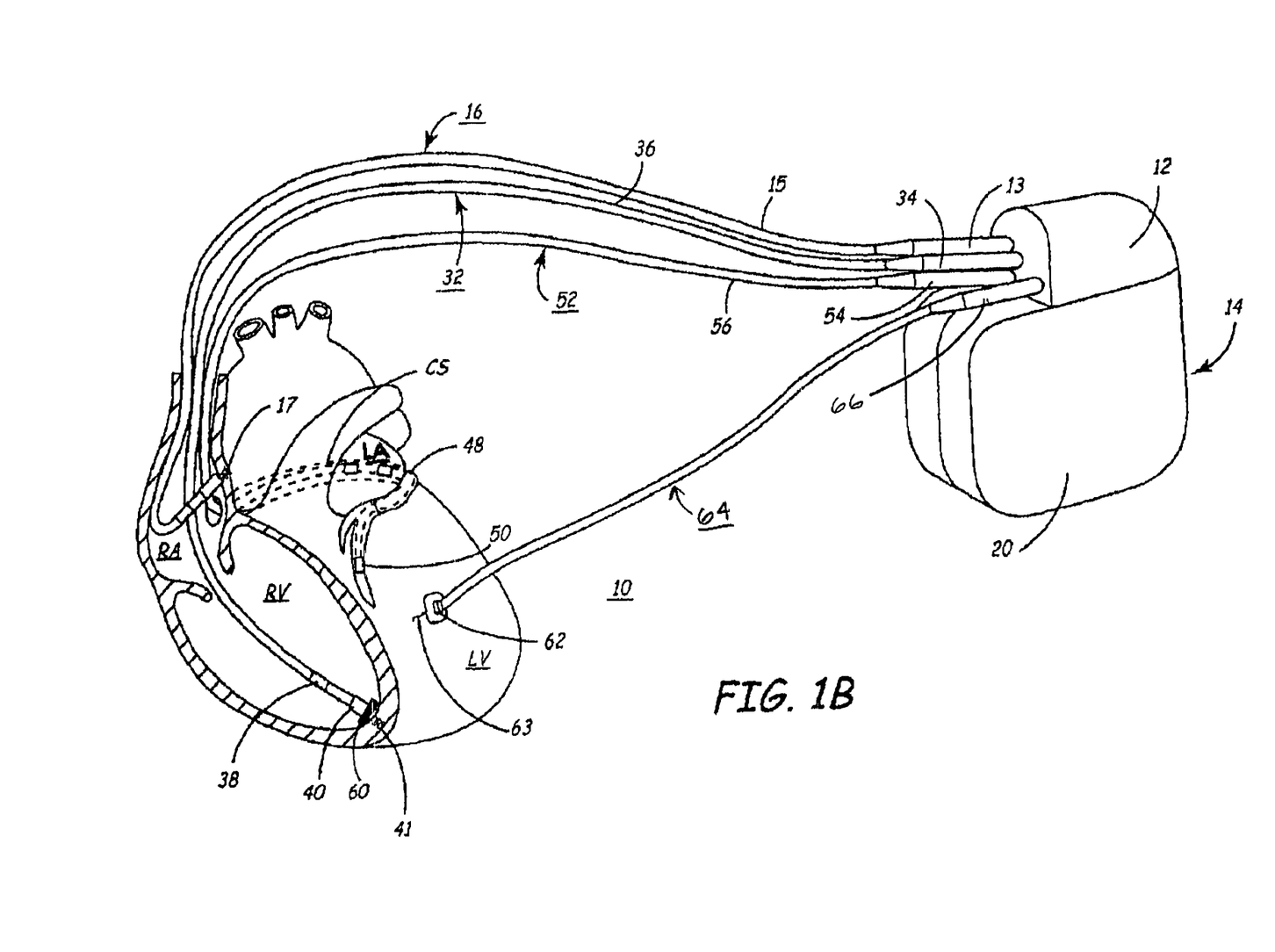
FIG. 1B depicts an implantable, multi-chamber cardiac pacemaker coupled to a patient's heart via transvenous endocardial leads and an additional left ventricular epicardial lead equipped with acceleration sensor.

FIG. 1B depicts an implantable, multi-chamber cardiac pacemaker coupled to a patient's heart via transvenous endocardial leads and an additional left ventricular epicardial lead equipped with acceleration sensor 62. Patients may have previously had a transvenous lead system implanted that includes a coronary sinus lead 52 that is not equipped with an acceleration sensor. Such patients may benefit from the placement of an epicardial lead 64 equipped with an acceleration sensor 62 coupled to IMD 14 via a connector 66 so as to provide an LV acceleration signal.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for stimulation, EGM sensing and acceleration sensing, thereby eliminating the need for a coronary sinus lead. Alternatively, it may be desirable to deploy a small diameter coronary sinus lead for LV stimulation and EGM sensing with a separate LV epicardial lead positioned for sensing LV acceleration.

The embodiment generally shown in FIG. 1B may be used for specific selection of cardiac stimulation/sensing sites. With epicardial lead 64 fixed at a desired location for assessing LV acceleration, the effect of pacing at different locations in one or more heart chambers can be evaluated by deploying the transvenous pacing leads 16, 32 and 52 to different locations. In particular, coronary sinus lead 52 may be advanced to different locations until an optimal location is identified based on analysis of the signal from LV acceleration sensor 62. By providing acceleration sensor 62 on a separate, epicardial lead 64, the position of LV pace/sense electrode 50, provided on coronary sinus lead 52, may be adjusted independently of sensor 62. If the position of pace/sense electrode 50 needs adjusting, acceleration sensor 62 may remain fixed at a desired measurement site on the LV epicardial wall thereby allowing comparisons to be made between measurements repeated at the same location for different pacing intervals and/or pacing sites.

Any type of transducer may be provided for sensing or deriving ventricular wall acceleration corresponding to the right and/or left ventricle provided such transducers are hermetically sealed, fabricated (at least on the exterior surfaces) of substantially biocompatible materials and appropriately dimensioned for a given application. In addition to transducers that sense acceleration, transducers which sense velocity, displacement or force may be used from which an acceleration component can be derived. With respect to appropriate dimension, a transducer intended for transvenous deployment should be adapted for catheter or over-the-wire delivery. Thus, the radial dimension should generally be on the order of less than about 11 French. The transducer should be somewhat supple with a longitudinal dimension that allows the transducer to safely navigate the venous system, pass through the coronary sinus and enter vessels branching from the coronary sinus. These dimensions are less limited for a transducer intended for deployment though a portion of the chest (e.g., a thoracotomy) with a fixation mechanism adapted to mechanically coupled adjacent the epicardium or pericardium. The dimensions may be relaxed to a greater extent if the epicardial receives the transducer, and to a lesser extent, to a portion of the pericardium. As is well known, the pericardium is the membranous sac filled with serous fluid that encloses the heart and the roots of the aorta and other large blood vessels. One example of appropriate fixation apparatus for epicardial application is a lead having a distal fixation helix that is screwed into the surface of the epicardium. For pericardial fixation a sealing member (e.g., compressible gasket or opposing members on each side of the pericardial sac) may be used in addition to an active fixation member such as a helical member.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electrical signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describes the internal mechanism of the accelerometer, includes a spring-retained seismic mass. In most accelerometers, acceleration forces a damped seismic mass that is restrained by a spring, so that it moves relative to the transducer casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20-60 Hz, depending on the stiffness of the spring, and have a high-level output signal. They also have a lower frequency response than most other accelerometers, usually between 15-30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

Figure 2:
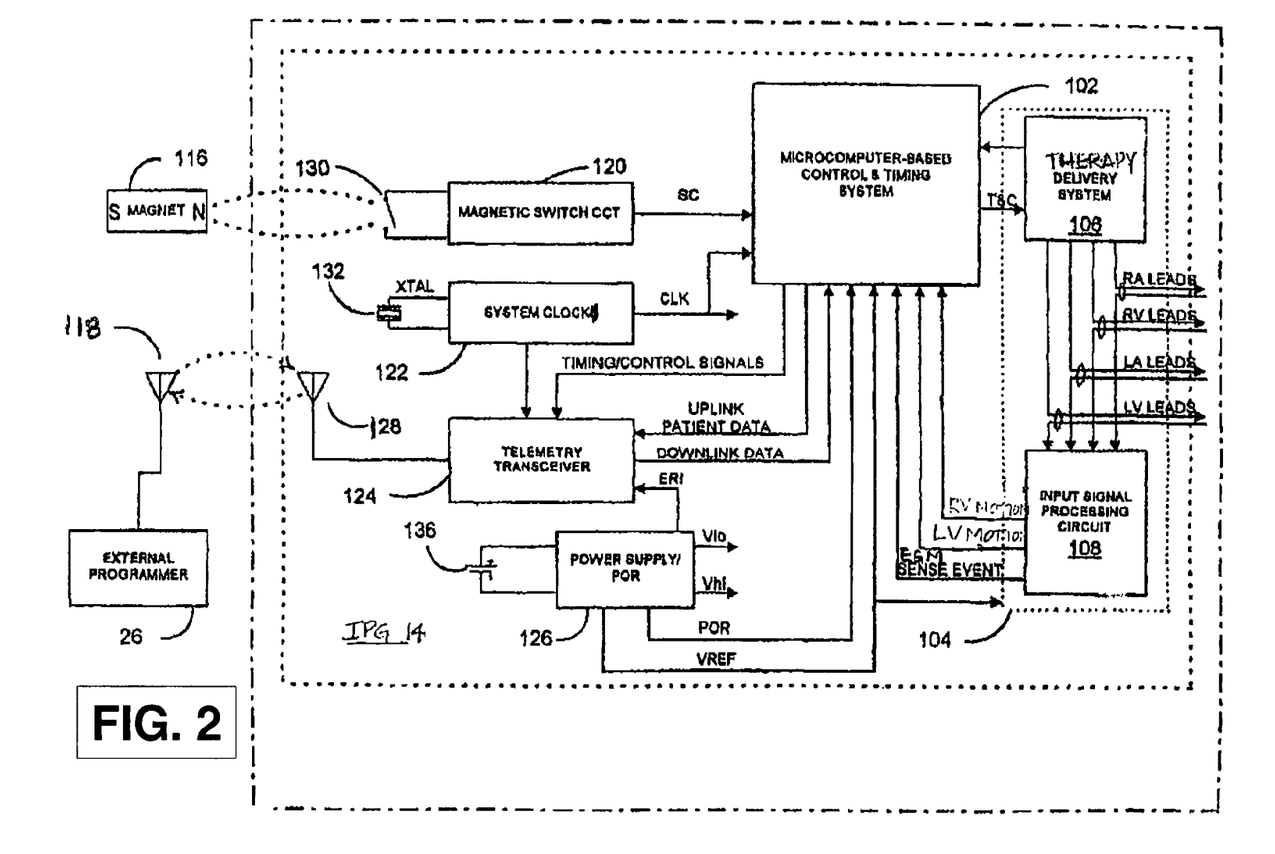
FIG. 2 is a schematic block diagram illustrating one embodiment of a multi-chamber IMD.

FIG. 2 is a schematic block diagram illustrating one embodiment of a multi-chamber IMD 14. IMD 14 is configured to provide a cardiac stimulation therapy and for processing ventricular acceleration signal input from any of the types of transducers described above or any other type of transducer sensitive to ventricular acceleration for use in performing atrial EMD measurements. In some embodiments, as will be described herein, IMD 14 measures inter-atrial EMD and/or intra-atrial EMD using sensed atrial electrical and mechanical events. IMD 14 may store EMD data for diagnostic and monitoring purposes. IMD 14 may additionally or alternatively use EMD data for setting timing parameters used to control cardiac stimulation pulse delivery.

As shown, IMD 14 includes a microprocessor-based control and timing system 102 for controlling the functions of IMD 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IMD 14 can be accomplished with dedicated circuit hardware or state machine logic rather than a programmed microcomputer.

The IMD 14 includes interface circuitry 104 for receiving signals from sensors and pace/sense electrodes located at specific sites of the patient's heart chambers and delivering cardiac stimulation aimed at achieving a therapeutic benefit. The interface circuitry 104 therefore includes a therapy delivery system 106 intended for delivering cardiac stimulation pulses under the control of control and timing system 102. Delivery of stimulation pulses in one or more heart chambers is controlled in part by the selection of programmable timing intervals, which can include atrial-atrial (A-A), atrial-ventricular (A-V), and ventricular-ventricular (V-V) intervals and may further include extra systolic intervals or other timing intervals according to the type of therapy being delivered and the programmed operating mode.

Physiologic input signal processing circuit 108 is provided for receiving cardiac electrogram (EGM) signals for determining a patient's heart rhythm. Physiologic input signal processing circuit 108 additionally receives signals from left ventricular acceleration sensor 62, and/or RV acceleration sensor 60, processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV. In other embodiments, far-field electrodes, for example electrodes implanted subcutaneously or incorporated in the housing of IMD 14 may be used in sensing ECG signals received by physiologic input signal processing circuit 108.

Control and timing system 102 controls the delivery cardiac stimulation pulses at selected timing intervals intended to improve heart function or otherwise alleviate a heart condition as needed. Selection of the programmable intervals may include an analysis of atrial EMD as will be described in greater detail below.

The therapy delivery system 106 can optionally be configured to include circuitry for delivering cardioversion/defibrillation therapy in addition to cardiac pacing pulses. Accordingly, leads in communication with the patient's heart could additionally include high-voltage cardioversion or defibrillation shock electrodes.

A battery 136 provides a source of electrical energy to power components and circuitry of IMD 14 and provide energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. A power supply and interconnections with IMD 14 components may correspond to configurations known in the art.

Electronic IMD circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM/ECG signals, ventricular acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including ventricular acceleration data and data derived there from such as atrial EMD data, or other excitation-physiologic response data, may be stored on a triggered or periodic basis or by detection logic within the physiologic input signal processing circuit 108. In some cases, the IMD 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IMD 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM/ECG, or ventricular wall acceleration data as well as real-time generated physiologic data and non-physiologic data can be transmitted by uplink RF telemetry from the IMD 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetric communication of both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM/ECG amplifier circuit for providing an EGM/ECG signal to the control and timing system 102 for sampling, digitizing and storing or transmitting in an uplink transmission. Atrial and ventricular sense amplifiers include signal processing stages for detecting the occurrence of atrial and ventricular depolarization and/or repolarization, respectively, and providing an atrial sense or ventricular sense event signal to the control and timing system 102. Atrial depolarization is sensed using any available near-field or far-field EGM/ECG signal for determining the time occurrence of atrial electrical activation for use in measuring atrial EMD. Ventricular depolarization is sensed in a similar manner.

Timing and control system 102 responds to sensed atrial and ventricular depolarizations in accordance with its particular operating mode to deliver or modify a stimulation therapy, if appropriate, or to accumulate data for uplink telemetry transmission in a variety of ways known in the art.

Thus the need for cardiac stimulation pulse delivery is generally determined based on EGM signal input according to the particular operating mode in effect. However, the intervals at which stimulation pulses are delivered may be determined, in some embodiments, based on atrial EMD measurements as will be described below.

The time occurrence of atrial mechanical contraction, used in measuring atrial EMD, is derived from a ventricular acceleration signal. As such, input signal processing circuit 108 further includes signal processing circuitry for receiving, amplifying, filtering, averaging, digitizing, synchronous averaging with respect to a specific event on the cardiac cycle or other triggering event or otherwise processing the LV and/or RV wall acceleration sensor signal. Acceleration signal processing circuitry is further provided for detection and/or determination of one or more acceleration signal characteristics such as maximum and minimum peak amplitudes, slopes, integrals, or other time or frequency domain signal characteristics that may be used in detecting atrial mechanical contraction.

Acceleration data from an LV wall acceleration sensor signal are made available to control and timing system 102 via LV MOTION signal line. LV acceleration data may be used for determining the time of LA mechanical contraction for use in measuring LA intra-atrial EMD and for use in measuring inter-atrial EMD. If an RV acceleration sensor is present, an additional RV MOTION signal line provides RV acceleration signal data to control and timing system 102. RV acceleration data may be used for determining the time of RA mechanical contraction for use in measuring RA intra-atrial EMD and may be used in some embodiments for measuring inter-atrial delay.

Other sensor signals may be provided to input signal processing circuit 108, such as blood pressure signals, blood chemistry signals, impedance signals, or other signals varying with or correlated to a physiological response subsequent to a cardiac electrical event. Such signals may be used in determining an excitation-physiologic response delay.

Figure 3:
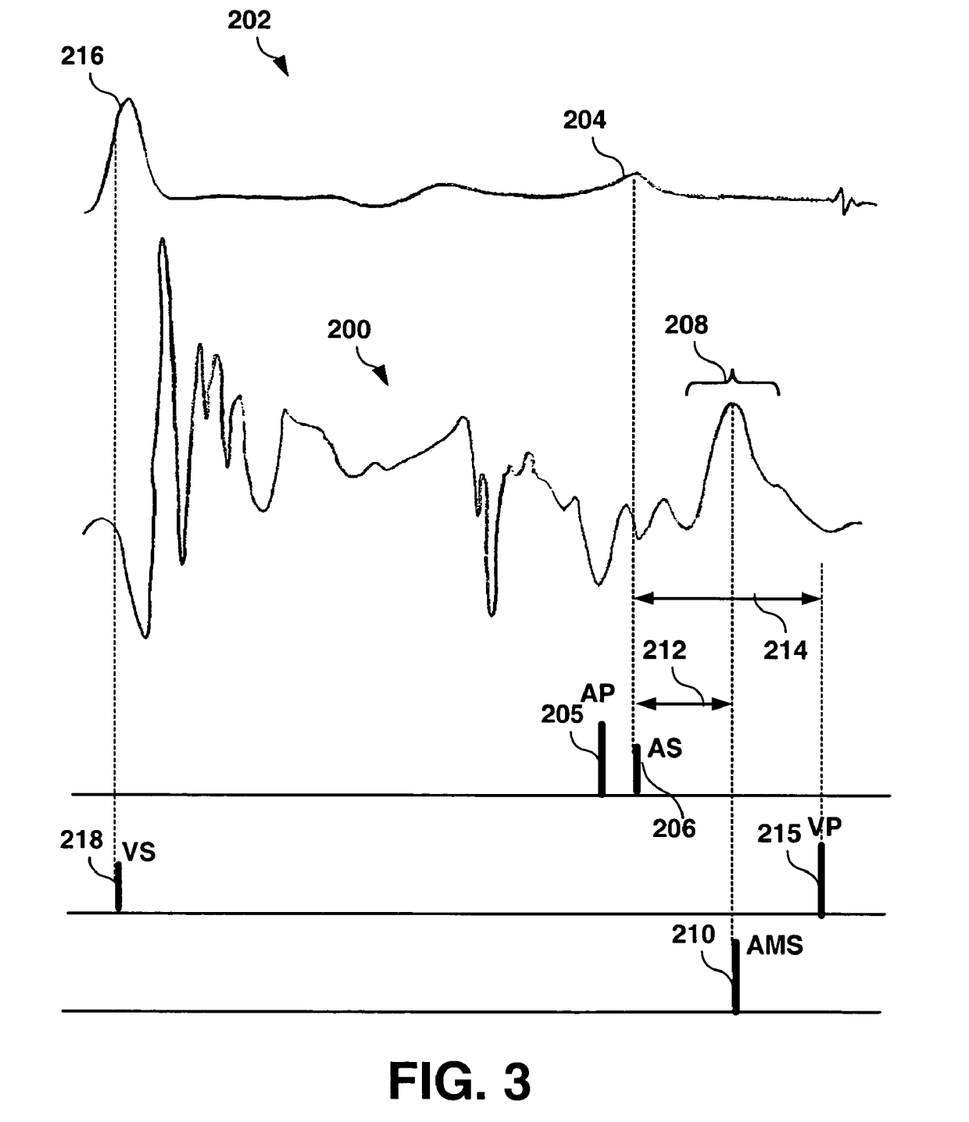
FIG. 3 shows an example of an ECG signal and an LV acceleration signal illustrating one method for measuring an atrial EMD.

FIG. 3 shows an example of an ECG signal and an LV acceleration signal illustrating one method for measuring an atrial EMD. The LV acceleration signal 200 is shown in time with simultaneously recorded ECG signal 202. A P-wave 204 occurring on the ECG signal 200 is sensed as an atrial electrical event 206 by the IMD. In the example shown, atrial electrical event 206 follows an atrial pacing pulse 205. However, an atrial electrical event used for measuring atrial EMD may be either a sensed evoked or intrinsic depolarization or an applied stimulus (e.g. pacing pulse). Any selected feature of the atrial depolarization signal may be detected as the electrical excitation event for use in measuring an EMD. In some embodiments, an electrical event used in measuring a physiologic response delay may be a detected feature of a repolarization signal. A ventricular acceleration signal peak 208 occurring on the acceleration signal 202 during cardiac diastole is evidence of LV filling due to LA contraction. As such, acceleration signal peak 208 may be sensed as an LA mechanical event 210 by the IMD. Acceleration signal peak 208, and other acceleration signals referred to herein, may be detected using a peak detection method for detecting the time of a maximum peak or may be detected based on the signal width, or any other characteristic feature of the signal. The atrial EMD 212 is measured as the time interval between the sensed atrial electrical event (atrial sense or AS) 206 and the sensed LA mechanical event (atrial mechanical sense or AMS) 210. During atrial pacing, the atrial EMD could alternatively be measured as the time interval between an atrial pacing pulse 205 and the sensed atrial mechanical event 210.

The atrial EMD 212 represents an inter-atrial EMD measurement since the P-wave 204 occurring on ECG signal 200 represents global atrial depolarization. The contributions of RA depolarization and LA depolarization to the ECG signal may vary depending on the ECG sensing electrode site. As such, the atrial electrical event sensed using a global ECG/EGM signal may be more specific to the RA or the LA depending on the ECG signal source. If a local RA EGM signal is available, for example using RA pace/sense electrodes 19 and/or 21 shown in FIG. 1, a more specific measurement of inter-atrial EMD may be made using the atrial depolarization sensed from the RA EGM signal and the LA mechanical event sensed from the LV acceleration signal.

In other embodiments, a local LA EGM signal may be available for measuring the LA intra-atrial EMD. The LA intra-atrial EMD is measured using a feature of the depolarization signal sensed in the LA and the LA mechanical event 210 sensed using a selected feature from the LV acceleration signal 200. Likewise, a local RA EGM signal may be available for measuring the RA intra-atrial EMD using an EGM-sensed electrical activation signal in the RA and a RA mechanical event sensed from an RV acceleration signal.

To facilitate detection of a ventricular acceleration signal corresponding to atrial contraction, the LV acceleration signal 200 may be sensed during a sensing window 214. Sensing window 214 may be initiated upon a delivered atrial pacing pulse 205 or a sensed atrial electrical event 206 or any other reliably detectable event indicating the onset of cardiac diastole or the ventricular filling phase. Sensing window 214 may extend for a predetermined time interval or until detection of an event indicating the end of diastole and onset of systole or ventricular contraction. For example, sensing window 214 may extend until a delivered ventricular pacing pulse 215, which may be a right or left ventricular pacing pulse, an intrinsic or evoked sensed ventricular event 218 corresponding to an R-wave 216 on ECG signal 202, an applied ventricular pacing pulse, or a sensed mechanical ventricular contraction. Other signals may be used for setting sensing window 214, such as other EGM signals, the LV acceleration signal 202 or other cardiac signals that may be available such as a pressure signal or an RV acceleration signal.

The atrial mechanical event 210 sensed using LV acceleration signal 202 may correspond to detecting a maximum peak of acceleration signal 208 during sensing window 214. Alternatively, sensing of atrial mechanical event 210 may be based on a threshold crossing, a peak-to-peak difference, a slope, or other reliably detectable feature of the acquired ventricular acceleration signal 200 that corresponds to atrial contraction. While the example shown in FIG. 3 is based on sensing an LV acceleration signal for sensing a LA mechanical event, it is understood that similar methods may be applied to sensing a RA mechanical event using an RV acceleration signal.

Figure 4:
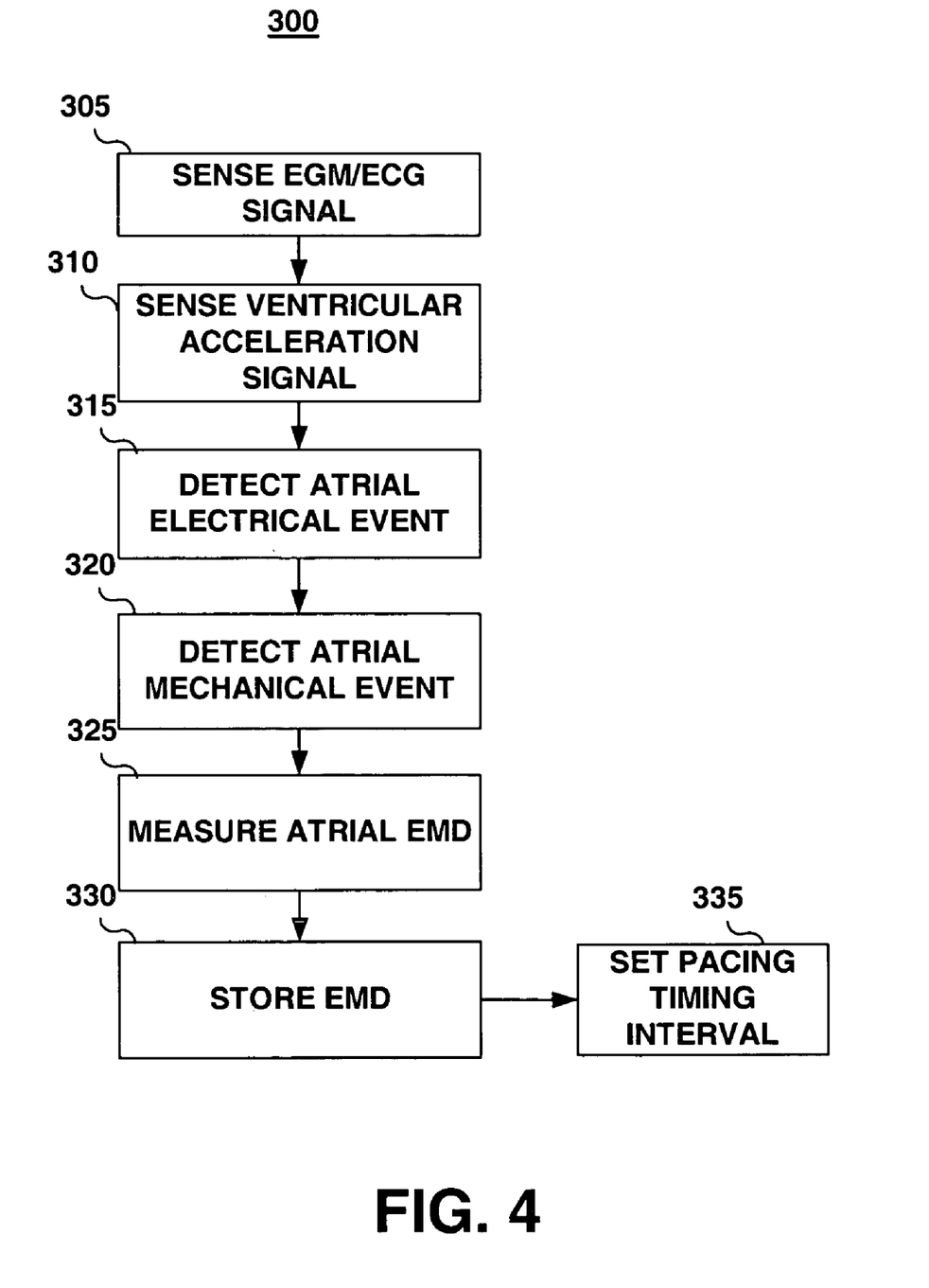
FIG. 4 is a flow chart summarizing steps included in one method for measuring atrial EMD.

FIG. 4 is a flow chart summarizing steps included in one method for measuring atrial EMD. At block 305, an EGM or ECG signal is sensed. As indicated above, the EGM/ECG signal may be a global signal used to detect a P-wave occurring upon atrial depolarization. Alternatively, a local EGM signal may be sensed for providing more specific timing information relating to the occurrence or a P-wave in the right or left ventricle. At block 310, a ventricular acceleration signal is sensed, which may be an RV or LV acceleration signal.

Using the sensed EGM/ECG signal, an atrial electrical event is detected at block 315. The atrial electrical event may be detected as any selected point on the atrial depolarization signal. Using the ventricular acceleration signal, an atrial mechanical event is sensed at block 320 using any selected point on the ventricular acceleration signal. The time interval between the atrial electrical event and the atrial mechanical event is measured as the atrial EMD at block 325. As described previously, the measured atrial EMD may be an intra-atrial EMD or an inter-atrial EMD depending on the particular EGM/ECG and ventricular acceleration signals used.

At block 330, the measured atrial EMD may be stored in IMD memory. The atrial EMD may be stored for monitoring purposes. A long atrial EMD may be a risk factor in atrial arrhythmias and may be useful in diagnosing atrial conditions. Stored atrial EMD data may be used in monitoring trends in atrial EMD for monitoring the progression of an atrial condition, such as atrial arrhythmia risk, or stretching or reverse remodeling of the atrial chamber.

At block 335, the atrial EMD may be used in optimizing a pacing timing interval such as AVI. Knowing the atrial EMD can be useful in setting the timing of atrial and ventricular pacing pulses in order to optimize atrial-ventricular coupling. During optimal atrial-ventricular coupling, the atrial contribution to ventricular filling occurs after passive ventricular filling and is not truncated by the onset of the ventricular contraction.

Figure 5:
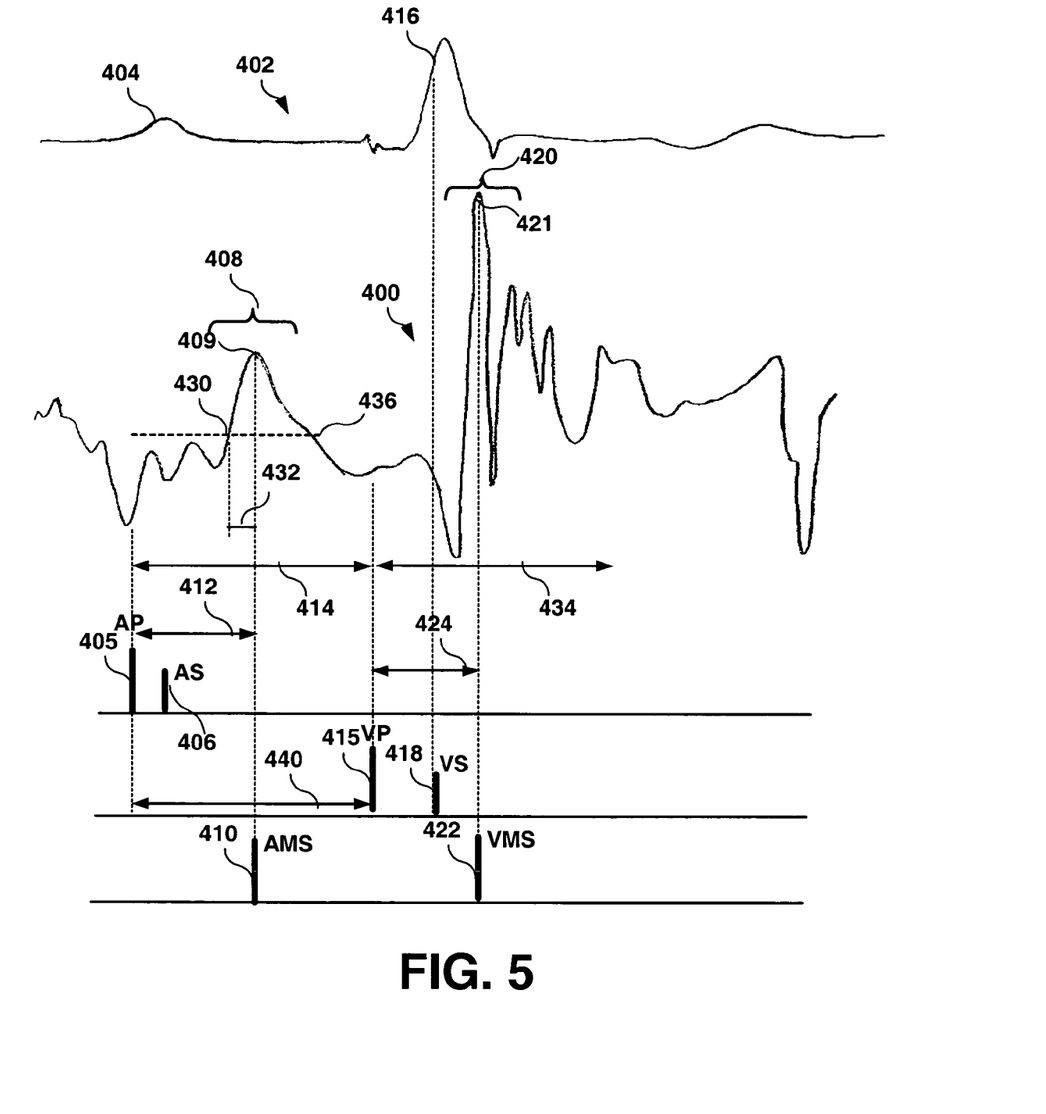
FIG. 5 shows an example of an ECG signal and an LV acceleration signal depicting atrial and ventricular electrical and mechanical events used in measuring an excitation-physiologic response delay.

FIG. 5 shows an example of an ECG signal and an LV acceleration signal illustrating one method for optimizing AV delay using a measurement of atrial EMD. Simultaneously recorded ECG signal 402 and LV acceleration signal 400 are shown. An atrial pacing pulse 405 precedes P-wave 404 on ECG signal 402. A ventricular pacing pulse 415 occurs after an AV delay 440 following atrial pacing pulse 405 and precedes R-wave 416 on ECG signal 402.

A feature of LV acceleration signal peak 408 occurring on acceleration signal 400 during diastolic sensing window 414 is sensed as an atrial mechanical event 410. For example, maximum peak 409 or threshold crossing 430 may be detected as an atrial mechanical event. Diastolic sensing window 414 in this embodiment begins at atrial pacing pulse 405 and ends at ventricular pacing pulse 415. The atrial EMD 412 is measured as the interval between the atrial pacing pulse 405 and the atrial mechanical event 410. It is recognized that the atrial EMD may alternatively be measured between an atrial electrical sensed event 406 corresponding to the occurrence of P-wave 404 or any detectable signal feature corresponding to atrial depolarization. The atrial EMD 412 may alternatively be measured as the interval between a selected depolarization signal feature and any feature of the LV acceleration signal peak, such as threshold crossing 430 which would correspond to the onset of the mechanical response.

A feature of LV acceleration signal peak 420 occurring on acceleration signal 400 during a second sensing window 434 is sensed as a ventricular mechanical event 422. Ventricular mechanical event 422 may be detected based on detection of the maximum peak 421, a threshold crossing, or any other characteristic feature of the signal peak 420. The second sensing window 434 is provided as a systolic sensing window starting from ventricular pacing pulse 415 and extending for a predetermined time interval there after. It is recognized that sensing window 434 may be defined with respect to any reliably detectable events corresponding to the onset of systole. A ventricular EMD 424 is measured as the interval between the ventricular pacing pulse 415 and the sensed ventricular mechanical event 422. The ventricular EMD may alternatively be measured between a ventricular electrical sensed event 418 corresponding to R-wave 416 and the ventricular mechanical event 422. Acceleration peak 420 corresponds to the isovolumic contraction phase of the LV. It is understood that other features of LV acceleration signal during systolic sensing window 434 may be detected as an LV mechanical event, such as a threshold crossing, a slope, an inflection point, or a minimum peak.

For optimal atrial-ventricular coupling, the onset of ventricular contraction should occur after atrial contraction is complete. Accordingly, it is desirable to estimate the end of atrial contraction. One method for estimating the end of atrial contraction includes estimating the onset of atrial contraction based on a threshold crossing 430 of LV acceleration peak 408 during sensing window 414. A half atrial contraction time 432 is estimated as the time interval between the threshold crossing 430 and the maximum peak 409 of acceleration peak 408. Alternatively, the half atrial contraction time is estimated as the time interval between the increasing threshold crossing 430 and the decreasing threshold crossing time 436. The total time required for the atrium to contract and relax may be estimated as twice the half atrial contraction time 432. The time at which the atrial contraction is complete after the delivery of an atrial pacing pulse 405 can be estimated as the atrial EMD 412 plus the half atrial contraction time 432. In alternative embodiments, the end of atrial contraction may be estimated based on a second, decreasing, threshold crossing time 436.

The onset of the isovolumic contraction phase of the ventricle should occur at or just after the completion of atrial contraction. Using the measurements illustrated in FIG. 5, an optimal AV delay may be computed as the atrial EMD 412 plus twice the half atrial contraction time 432 less the ventricular EMD 424. This optimal AV delay would result in delivery of a ventricular pacing pulse at a time prior to the estimated end of atrial contraction that equals the ventricular EMD. Ventricular contraction will be initiated after complete filling, without truncation of the atrial contribution to filling.

It is understood that in various embodiments, the optimal time point at which ventricular mechanical contraction should begin may be defined relative to different points identified on the atrial component of the acceleration signal 400. Selection of any time point, relative to the atrial mechanical sensed event 410, at which ventricular contraction should begin is within the scope of the invention. Generally, the onset of right ventricular contraction should occur upon closure of the tricuspid valve and left ventricular contraction should occur upon closure of the mitral valve. Any time point determined as a function of atrial EMD that minimizes the likelihood of the ventricular contraction beginning prior to valve closure may be selected.

Figure 6:
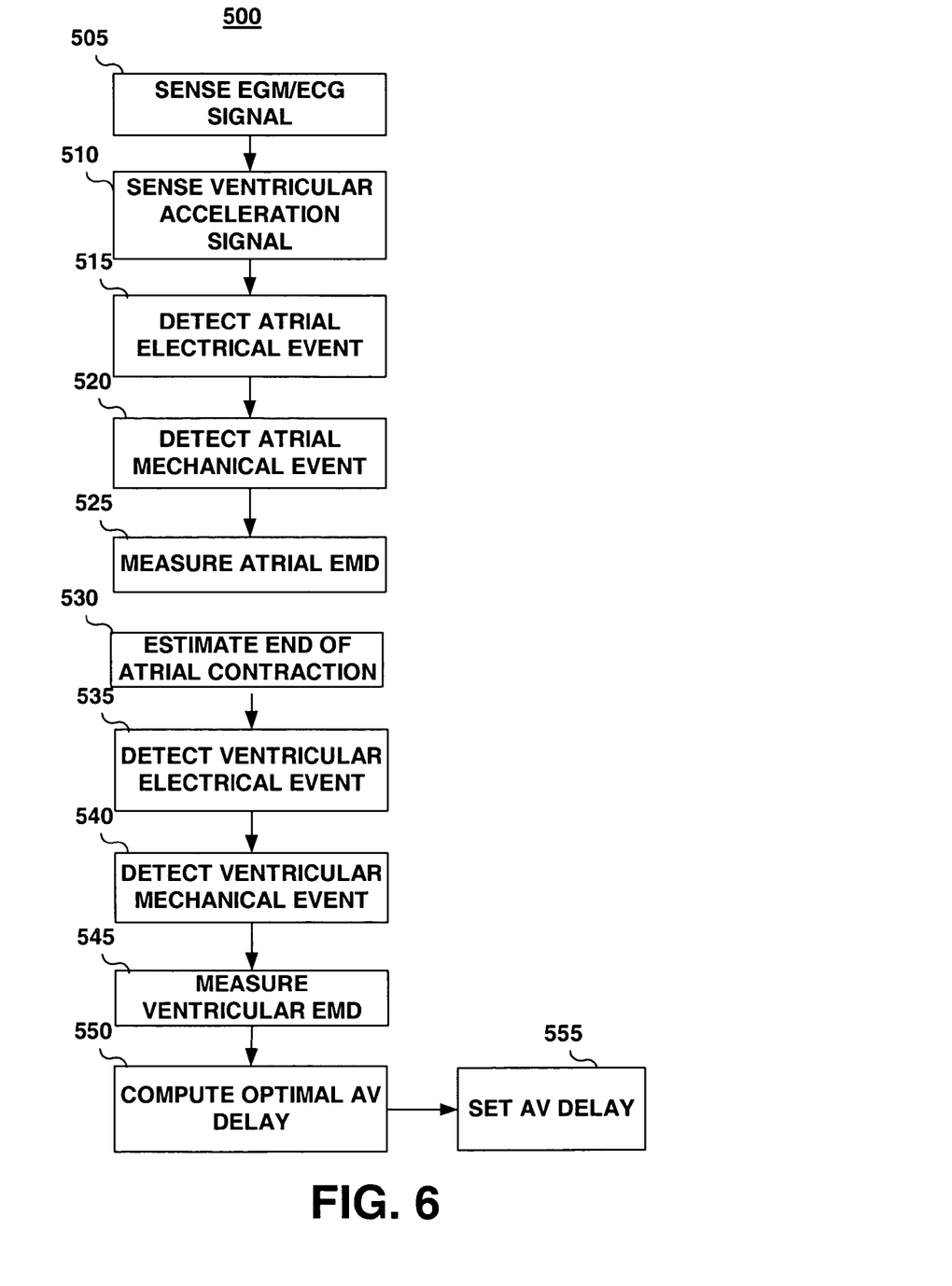
FIG. 6 is a flow chart summarizing one method for using atrial EMD measurements in setting an optimal AV delay.

FIG. 6 is a flow chart summarizing one method for using atrial EMD measurements in setting an optimal AV delay. At block 505 an EGM/ECG signal is sensed. A global EGM/ECG signal may sensed for allowing sensing of both P-waves and R-waves. Alternatively, local, near-field EGM signals may be sensed for sensing local P-waves and R-waves. At block 510 a ventricular acceleration signal is sensed. The ventricular acceleration signal may be an RV or LV acceleration signal.

At block 515, an atrial electrical event is detected for measuring the atrial EMD. The atrial electrical event may be a paced or sensed event. A subsequent atrial mechanical event is detected at block 520 using the sensed ventricular acceleration signal. The atrial EMD is measured at block 520 as the interval between the atrial electrical and mechanical events.

At block 530, the end of atrial contraction is estimated. The end of atrial contraction may be estimated as a fixed interval following the sensed atrial mechanical event or correspond to an additional time interval following the atrial mechanical event defined according to a threshold crossing, slope, inflection point or other feature of the ventricular acceleration signal that occurs during a diastolic sensing window. The end of atrial contraction may be estimated by determining a half atrial contraction time as described above and adding the half atrial contraction time to the measured atrial EMD.

At block 535, a ventricular electrical event, paced or sensed, is detected. At block 540 a ventricular mechanical event is detected. A ventricular mechanical event may be an acceleration signal peak occurring during a systolic sensing window, which corresponds to isovolumic contraction as described above. The ventricular EMD is measured at block 545 as the time interval between the ventricular electrical and mechanical events.

At block 550, an optimal AV delay is computed as a function of the atrial EMD, to minimize the likelihood of ventricular contraction beginning prior to the end of atrial contraction. In one embodiment, the optimal AV delay is computed as the atrial EMD (marking the beginning of atrial activity) plus twice the estimated half atrial contraction time less the ventricular EMD. The AV delay may be set at block 555 according to the optimal AV delay. In some embodiments, a safety margin may be added to the optimal AV delay to ensure ventricular contraction after atrial contraction (mitral or tricuspid valve closure) is complete.

Figure 7:
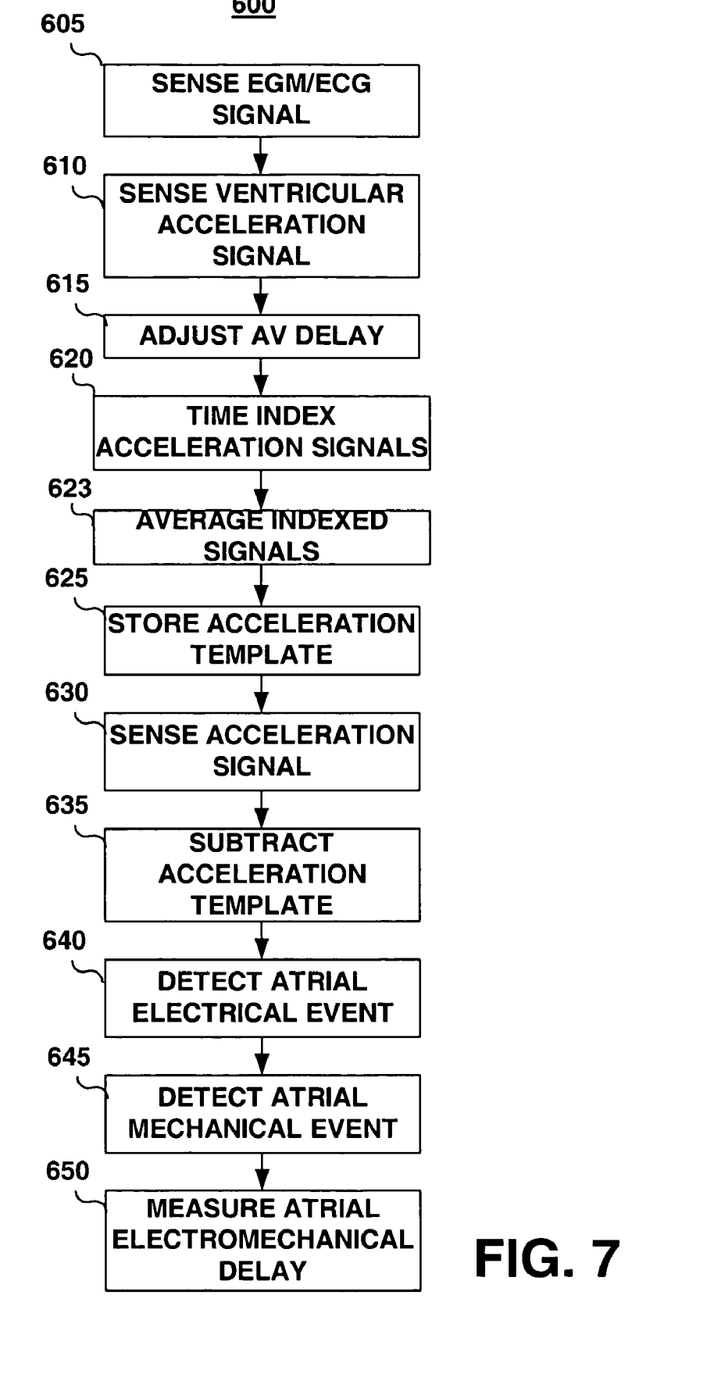
FIG. 7 is a flow chart summarizing one method for processing ventricular accelerometer signals for use in measuring atrial EMD.

FIG. 7 is a flow chart summarizing one method for processing ventricular accelerometer signals for use in measuring atrial EMD. At block 605, an EGM/ECG signal is sensed that allows ventricular electrical events to be detected. At block 610, a ventricular acceleration signal is sensed. The ventricular acceleration signal includes both atrial components and ventricular components as illustrated in FIG. 5. The ventricular acceleration signal will also include non-cardiac signal contributions due to other body motion such as respiratory motion. In order to clearly recognize the atrial components of the ventricular acceleration signal, it may be desirable to process the signal so as to remove ventricular and non-cardiac components of the signal.

At block 615, the AV delay is iteratively adjusted to a number of AV delay settings over a predetermined range of settings. The atrial EMD is expected to be relatively constant, independent of changing AV delay. Changes in AV delay can significantly change the atrial component of the acceleration since the atrial contraction may occur earlier or later in the filling phase. For example, when the atrial contraction occurs later in the filling phase, separate passive and active filling phases are observable associated with ventricular relaxation and atrial contraction, respectively. When the atrial contraction occurs earlier in the filling phase, a fused filling phase may be observed.

The acceleration signals obtained over each cardiac cycle are indexed in time relative to a ventricular electrical event (an R-wave sensed from the EGM/ECG signal or a pacing pulse) at block 620. The ventricular signal components will be aligned in time and are expected to have little variation due to changing AV delay. The ventricular pace or ventricular depolarization time-indexed acceleration signals are averaged at block 623 to obtain a ventricular acceleration template, which is stored at block 625. Time indexing can also be done with respect to other fixed fiducial point on the atrial or ventricular EGM to obtain other templates which can provide emphasis and quantification of local intra-cardiac event signatures. Since the atrial component of the ventricular accelerometer signal will change more than ventricular signal components during varying AV delay, averaging the time-indexed ventricular acceleration signal acquired during different AV delay settings will remove the atrial contributions. Other non-cardiac contributions such as respiratory contributions will also be removed by averaging the signals. The acceleration template will primarily represent the ventricular contributions to the acceleration signal when developed from averaging signals obtained during varying AV delays aligned to a ventricular event. Synchronous averaging or time indexed averaging of the processed or raw signals from a plurality of AV delays might also be done with respect to fiducial points on the atrial EGM to emphasize atrial effects.

At block 630, the ventricular acceleration signal is sensed for use in determining an atrial EMD. At block 635, the stored ventricular acceleration template is subtracted from the ventricular acceleration signal. The resulting difference signal includes the atrial components with the ventricular components removed. An atrial alignment indexed averaging could be done to emphasize the residual signal. At block 640 an atrial electrical event (paced or sensed) is detected. At block 645 an atrial mechanical event is detected using the acceleration signal with ventricular components removed. Detection of the atrial mechanical event may be more reliably performed using the signal filtered for non-atrial contributions by subtracting the acceleration template. At block 650, the atrial EMD is measured as the interval between the atrial electrical and mechanical events. It is realized that the signal processing methodology applied here could be used to emphasize specific cardiac events from other AV delay-responding sensor signals depending on the chosen indexing feature in the time-indexing signal.

Thus, a method and apparatus for measuring EMD and using EMD in optimizing pacing parameter have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device system, comprising:
    sensing a first signal responsive to electrical activity in a first cardiac chamber, wherein the first cardiac chamber is a first atrial chamber;
    sensing a second signal responsive to a physiologic response to the electrical activity in the first cardiac chamber, wherein the second signal is a ventricular wall acceleration signal; and
    determining an excitation-physiologic response delay in response to the first signal and the second signal, wherein determining the excitation-physiologic response delay includes sensing an atrial electrical event in response to the first signal, sensing an atrial mechanical response to the atrial electrical event in response to the second signal, and determining a time interval between the atrial electrical event and the atrial mechanical response.

2. A method according to claim 1 wherein the atrial mechanical event occurs in a second atrial chamber.

3. A method according to claim 1 wherein sensing the first signal includes detecting one of an electrical depolarization signal feature and an electrical repolarization signal feature.

4. A method according to claim 1 wherein sensing the second signal includes sensing a signal responsive to one of a ventricular wall acceleration, a blood pressure, a blood chemistry, or an impedance.

5. A method according to claim 1 further including determining an optimal atrial-ventricular (AV) delay in response to the excitation-physiologic response delay.

6. A method according to claim 5 wherein determining the optimal AV delay includes estimating an atrial contraction end time based on the determined excitation-physiological response delay.

7. A method according to claim 5 wherein determining an optimal AV delay includes determining a ventricular electro-mechanical delay.

8. A method for use in an implantable medical device system, comprising:
    sensing a first signal responsive to electrical activity in a first cardiac chamber, wherein the first cardiac chamber is a first ventricular chamber;
    sensing a second signal responsive to a physiologic response to the electrical activity in the first cardiac chamber, wherein the second signal is a ventricular wall acceleration signal; and
    determining an excitation-physiologic response delay in response to the first signal and the second signal, wherein determining the excitation-physiologic response delay includes sensing a ventricular electrical event in response to the first signal, sensing a ventricular mechanical response to the ventricular electrical event in response to the second signal, and determining a time interval between the ventricular electrical event and the ventricular mechanical response.

9. A method according to claim 8 wherein the ventricular mechanical response to the electrical activity in the first ventricular chamber occurs in a second ventricular chamber.

10. A method for use in an implantable medical device system, comprising:
    sensing a first signal responsive to electrical activity in a first cardiac chamber;
    sensing a second signal responsive to a physiologic response to the electrical activity in the first cardiac chamber; and
    determining an excitation-physiologic response delay in response to the first signal and the second signal, wherein determining the excitation-physiologic response delay includes averaging the second signal over a number of cardiac cycles.

11. A method according to claim 10 wherein determining the excitation-physiologic response delay includes determining a second signal template wherein determining the second signal template includes: sensing the second signal during a plurality of atrial-ventricular (AV) delays, indexing the second signal sensed during the plurality of AV delays in time, and averaging the indexed second signal.

12. A method according to claim 11 wherein indexing the second signal includes aligning the second signal with a feature of the first signal.

13. A method according to claim 11 wherein determining the excitation-physiologic response delay includes subtracting the second signal template from the sensed second signal.

14. A computer-readable medium for storing a set of instructions which when implemented in an implantable medical device cause the device to:
    sense a first signal responsive to electrical activity in a first cardiac chamber;
    sense a second signal responsive to a physiologic response to the electrical activity in the first cardiac chamber; and
    determine an excitation-physiologic response delay in response to the first signal and the second signal, wherein determining the excitation-physiologic response delay includes averaging the second signal over a number of cardiac cycles.

15. An implantable medical device system, comprising:
- a first sensor for sensing a first signal responsive to electrical activity in a first cardiac chamber, wherein the first cardiac chamber is a first atrial chamber;
- a second sensor for sensing a second signal responsive to a physiologic response to the electrical activity in the first cardiac chamber, the second signal is a ventricular wall acceleration signal; and
- a processor for determining an excitation-physiologic response delay in response to the first sensor signal and the second sensor signal, wherein determining the excitation-physiologic response delay includes sensing an atrial electrical event in response to the first signal, sensing an atrial mechanical response to the atrial electrical event in response to the second signal, and determining a time interval between the atrial electrical event and the atrial mechanical response.

16. A system according to claim 15 wherein the atrial mechanical event occurs in a second atrial chamber.

17. An implantable medical device system, comprising:
- a first sensor for sensing a first signal responsive to electrical activity in a first cardiac chamber, wherein the first cardiac chamber is a first ventricular chamber;
- a second sensor for sensing a second signal responsive to a physiologic response to the electrical activity in the first cardiac chamber, wherein the second signal is a ventricular wall acceleration signal; and
- a processor for determining an excitation-physiologic response delay in response to the first sensor signal and the second sensor signal, wherein determining the excitation-physiologic response delay includes sensing a ventricular electrical event in response to the first signal, sensing a ventricular mechanical response to the ventricular electrical event in response to the second signal, and determining a time interval between the ventricular electrical event and the ventricular mechanical response.

18. A system according to claim 17 wherein the ventricular mechanical response to the electrical activity in the first ventricular chamber occurs in a second ventricular chamber.

19. A system according to claim 17 wherein sensing the first signal includes detecting one of an electrical depolarization signal feature and an electrical repolarization signal feature.

20. A system according to claim 17 wherein sensing the second signal includes sensing a signal responsive to one of a ventricular wall acceleration, a blood pressure, a blood chemistry, or an impedance.

21. A system according to claim 17 wherein the processor further determines an optimal atrial-ventricular (AV) delay in response to the excitation-physiologic response delay.

22. A system according to claim 21 wherein determining the optimal AV delay includes estimating an atrial contraction end time based on the determined excitation-physiological response delay.

23. A system according to claim 21 wherein determining an optimal AV delay includes determining a ventricular electromechanical delay.

24. An implantable medical device system, comprising:
- a first sensor for sensing a first signal responsive to electrical activity in a first cardiac chamber;
- a second sensor for sensing a second signal responsive to a physiologic response to the electrical activity in the first cardiac chamber; and
- a processor for determining an excitation-physiologic response delay in response to the first sensor signal and the second sensor signal, wherein determining the excitation-physiologic response delay includes averaging the second signal over a number of cardiac cycles.

25. A system according to claim 24, wherein determining the excitation-physiologic response delay includes determining a second signal template wherein determining the second signal template includes: sensing the second signal during a plurality of atrial-ventricular (AV) delays, indexing the second signal sensed during the plurality of AV delays in time, and averaging the indexed second signal.

26. A system according to claim 25 wherein indexing the second signal includes aligning the second signal with a feature of the first signal.

27. A system according to claim 25 wherein determining the excitation-physiologic response delay includes subtracting the second signal template from the sensed second signal.

28. A method for use in an implantable medical device system, comprising:
- sensing a first signal responsive to electrical activity in a first cardiac chamber;
- sensing a second signal responsive to a physiologic response to the electrical activity in the first cardiac chamber during a plurality of atrial-ventricular (A-V) delays;
- time-indexing the second signal during the plurality of AV delays to a selected feature of the first signal; and
- determining a second signal template by averaging the time-indexed second signal.

* * * * *